United States Patent [19]

Durette et al.

[11] Patent Number: 5,227,467

[45] Date of Patent: Jul. 13, 1993

[54] IMMUNOSUPPRESSIVE FLUORINATED CYCLOSPORIN ANALOGS

[75] Inventors: Philippe L. Durette, New Providence; Arsenio A. Pessolano, Colonia; Janos Kollonitsch, Westfield, all of N.J.

[73] Assignee: Merck & Co., Inc., Rahway, N.J.

[21] Appl. No.: 693,783

[22] Filed: Apr. 29, 1991

Related U.S. Application Data

[63] Continuation of Ser. No. 298,712, Jan. 19, 1989, abandoned, which is a continuation-in-part of Ser. No. 81,255, Aug. 3, 1987, abandoned.

[51] Int. Cl.$^5$ .................... C07K 7/64; A61K 37/02
[52] U.S. Cl. .................... 530/321; 530/317
[58] Field of Search .................... 530/317, 321; 514/9, 514/11, 885

[56] References Cited

U.S. PATENT DOCUMENTS

| | | | |
|---|---|---|---|
| 4,102,877 | 7/1978 | Nutt | 530/317 |
| 4,108,985 | 8/1978 | Ruegger et al. | 530/321 |
| 4,117,118 | 9/1978 | Harri et al. | 530/321 |
| 4,210,581 | 7/1980 | Ruegger et al. | 530/321 |
| 4,220,641 | 9/1980 | Traber et al. | 530/317 |
| 4,288,431 | 9/1981 | Traber et al. | 530/321 |
| 4,289,851 | 9/1981 | Traber et al. | 530/321 |
| 4,384,996 | 5/1983 | Bollinger et al. | 530/321 |
| 4,396,542 | 8/1983 | Wenger | 530/321 |
| 4,639,434 | 1/1987 | Wenger et al. | 530/321 |
| 4,649,047 | 3/1987 | Kaswan | 514/11 |
| 4,681,754 | 7/1987 | Siegl | 514/11 |
| 4,703,033 | 10/1987 | Seebach | 514/11 |
| 4,737,487 | 4/1988 | Watts et al. | 514/15 |
| 4,798,823 | 1/1989 | Witzel | 514/11 |
| 4,885,276 | 12/1989 | Witzel | 514/11 |
| 4,914,188 | 4/1990 | Dumont et al. | 530/317 |

FOREIGN PATENT DOCUMENTS 194972A 8/1986 European Pat. Off. .

OTHER PUBLICATIONS

Cram et al., Organic Chemistry, 2nd Edition, McGraw-Hill Book Company, New York, pp. 607-613 (1964).

Talmadge et al., 13th International Congress of Chemotherapy, Herberman et al. (ed.), Vienna, pp. 203/18-205/35 (1983).

H. Kobel and R. Traber, Directed Biosynthesis of Cyclosporins, European J. Appln. Microbiol Biotechnol., 14, 237-240 (1982).

J. Kollonitsch, Isr. J. Chem., 17, 53-59, (1978).

R. Wenger, Cyclosporine vol. 2, pp. 14-25 (1983).

R. Wenger, Total Synthesis-Change in Molecular Structure-Biological Effect: Cyclosporin as Example, Sandorama, 1984/111, pp. 4-11.

R. M. Wenger, Synthesis of Cyclosporine and Analogues; Structural Requirements for Immunosuppressive Activity, Angewandte Chemie 24:2, 77-138 (Feb., 1985).

*Primary Examiner*—Y. Christina Chan
*Attorney, Agent, or Firm*—Curtis C. Panzer; Raymond M. Speer

[57] ABSTRACT

New immunosuppressive cyclosporin analogs are disclosed having one or more fluorinated amino acids. These analogs may also have a "C-9 amino acid" wherein the double bond is replaced by a heteroatom such as sulfur or oxygen.

2 Claims, No Drawings

IMMUNOSUPPRESSIVE FLUORINATED CYCLOSPORIN ANALOGS

RELATED U.S. APPLICATION DATA

This is a continuation of application Ser. No. 298,712 filed Jan. 19, 1989 (now abandoned), which is a continuation-in-part of U.S. application Ser. No. 081,255, filed Aug. 3, 1987 (now abandoned).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents, such as NSAID's (Non-Steroidal Anti-inflammatory Drugs), and corticosteroids act principally by blocking the effect of, or secretion of, these mediators, but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb to infection as they are to their autoimmune disease.

The cyclosporins are a family of immunosuppressive compounds isolated from fermentation broths of various fungal species, including *Tolypocladium inflatum* and *Cyclindrocarpon lucidum*.

The generic structure of the class of cyclosporins has been established as a cyclic peptide of formula I, which contains 11 amino acids.

$$R^{10}-R^{11}-R^1-R^2-R^3$$
$$|\qquad\qquad\qquad\qquad|$$
$$R^9\qquad\qquad\qquad\qquad|$$
$$|\qquad\qquad\qquad\qquad|$$
$$R^8-R^7-R^6-R^5-R^4$$

(I)

Cyclosporin A, for example, shown below in formula II, contains seven N-methylated amino acids. One novel amino acid at position-1, "MeBmt", has been found to be important for the biological activity of cyclosporin. (The amino acid at position-1 is also known as the "C-9 amino acid"). We have previously found that replacing the double bond of the "C-9 amino acid" (MeBmt) with a heteroatom, such as Sulfur or Oxygen, decreases the toxicity of the parent cyclosporin. We have now found that fluorinating the amino acid at positions 2, 4, 5, 6, 7, 9, 10 and/or 11 around the ring provides potent immunosuppressive compounds, and unexpectedly in some cases, biological activity greater than that measured for cyclosporin A itself.

Biological activity is measured in terms of binding affinity for cyclophilin, the cytosolic receptor for cyclosporin (R. Handschumacher et al., Science, 226 (1984) 544), inhibition of interleukin-2 production, and inhibition of T-cell proliferation.

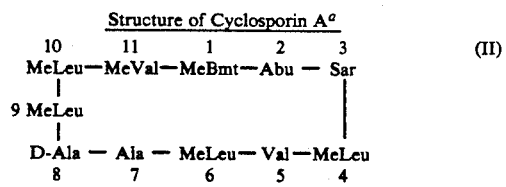

Structure of Cyclosporin A<sup>a</sup> (II)

```
  10      11      1       2      3
MeLeu—MeVal—MeBmt—Abu — Sar
  |                            |
9 MeLeu                        |
  |                            |
D-Ala — Ala — MeLeu— Val —MeLeu
  8       7       6      5      4
```

Abu = L-α-Aminobutyric acid
Ala = L-Alanine
Bmt = (4R)-4-[(E)-2-butenyl]-4-methyl-L-threonine
Leu = L-Leucine
Me = Methyl
MeLeu = N-Methyl-L-leucine
MeVal = N-Methyl-L-valine
Nva = L-Norvaline
Sar = Sarcosine
Thr = L-Threonine
Val = L-Valine <sup>a</sup>Unless otherwise specified, each of the amino acids of the disclosed cyclosporin is of the L-configuration.

Generally, a cyclosporin, such as cyclosporin A, is not cytotoxic nor myelotoxic. It does not inhibit migration of monocytes nor does it inhibit granulocytes and macrophage action. Its action is specific and leaves most established immune responses intact. However, it is nephrotoxic and is known to cause the following undesirable side effects:

(1) abnormal liver function;
(2) hirsutism;
(3) gum hypertrophy;
(4) tremor;
(5) neurotoxicity;
(6) hyperaesthesia; and
(7) gastrointestinal discomfort.

Accordingly, an object of the present invention is to provide a cyclosporin analog for the care of immunoregulatory disorders and diseases, including the prevention, control and treatment thereof.

An object of the present invention is to provide new cyclosporin analogs which will (1) restore the balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory diseases by administering a sufficient amount of one or more of the novel immunosuppressive agents in a mammalian species in need of such treatment.

Finally, it is the object of this invention to provide processes for the preparation of the active compounds of the present invention.

A number of cyclosporins and analogs have been described in the patent literature:

U.S. Pat. No. 4,108,985 issued to Ruegger, et al. on Aug. 22, 1978 entitled, "Dihydrocyclosporin C", discloses dihydrocyclosporin C, which can be produced by hydrogenation of cyclosporin C.

U.S. Pat. No. 4,117,118 issued to Harri, et al. on Sep. 26, 1978 entitled, "Organic Compounds", discloses cyclosporins A and B, and the production thereof by fermentation.

U.S. Pat. No. 4,210,581 issued to Ruegger, et al. on Jul. 1, 1980 entitled, "Organic Compounds", discloses cyclosporin C and dihydrocyclosporin C which can be produced by hydrogenation of cyclosporin C.

U.S. Pat. No. 4,220,641, issued to Traber, et al. on Sep. 2, 1980 entitled, "Organic Compounds", discloses cyclosporin D, dihydrocyclosporin D, and isocyclosporin D.

U.S. Pat. No. 4,288,431 issued to Traber, et al. on Sep. 8, 1981 entitled, "Cyclosporin Derivatives, Their Production and Pharmaceutical Compositions Containing Them", discloses cyclosporin G, dihydrocylosporin G, and isocyclosporin G.

U.S. Pat. No. 4,289,851, issued to Traber, et al. on Sep. 15, 1981 entitled, "Process for Producing Cyclosporin Derivatives", discloses cyclosporin D, dihydrocyclosporin D, and isocyclosporin D, and a process for producing same.

U.S. Pat. No. 4,384,996, issued to Bollinger, et al. on May 24, 1983 entitled "Novel Cyclosporins", discloses cyclosporins having a β-vinylene-α-amino acid residue at the 2-position and/or a β-hydroxy-α-amino acid residue at the 8-position. The cyclosporins disclosed included either MeBmt or dihydro-MeBmt at the 1-position.

U.S. Pat. No. 4,396,542, issued to Wenger on Aug. 2, 1983 entitled, "Method for the Total Synthesis of Cyclosporins, Novel Cyclosporins and Novel Intermediates and Methods for their Production", discloses the synthesis of cyclosporins, wherein the residue at the 1-position is either MeBmt, dihydro-MeBmt, and protected intermediates.

U.S. Pat. No. 4,639,434, issued to Wenger, et al on Jan. 27, 1987, entitled "Novel Cyclosporins", discloses cyclosporins with substituted residues at positions 1, 2, 5 and 8.

U.S. Pat. No. 4,681,754, issued to Siegel on Jul. 21, 1987 entitled, "Counteracting Cyclosporin Organ Toxicity", discloses methods of use of cyclosporin comprising co-dergocrine.

U.S. Pat. No. 4,703,033 issued to Seebach on Oct. 27, 1987 entitled, "Novel Cyclosporins", discloses cyclosporins with substituted residues at positions 1, 2 and 3. The substitutions at position-3 include halogen.

H. Kobel and R. Traber, *Directed Biosynthesis of Cyclosporins*, European J. Appln. Microbiol Biotechnol., 14, 237-240 (1982), discloses the biosynthesis of cyclosporins A, B, C, D & G by fermentation.

R. Wenger, *Total Synthesis—Change in Molecular Structure—Biological Effect: Cyclosporin as Example*, Sandorama, 1984/111, pages 4-11, discloses methods of production of cyclosporin A.

Additional cyclosporin analogs are disclosed in a copending U.S. patent application Ser. No. 057,196 filed by B. E. Witzel on Jun. 3, 1987 (now U.S. Pat. No. 4,798,823) entitled, "New Cyclosporin Analogs with Modified "C-9 amino acids," which discloses cyclosporin analogs with sulfur-containing amino acids at position-1.

None of the above references discloses the inventive cyclosporins disclosed hereunder.

SUMMARY OF THE INVENTION

This invention relates to novel cyclosporin analogs useful as immunosuppressive drugs. More specifically, this invention relates to cyclosporin analogs having one or more fluorinated amino acids at positions 2, 4 to 7, and 9 to 11. These cyclosporins may also have heteroatom-containing "C-9 amino acids".

DETAILED DESCRIPTION OF THE INVENTION

For purposes of this application, "fluorinated analog" shall be defined as an amino acid residue in which one or more of the various C—H bonds in the side chain are replaced with C—F bonds; for example, fluorinated analog of Abu represents

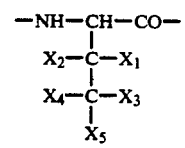

wherein $X_1$-$X_5$ independently is H or F with the proviso that at least one of $X_1$, $X_2$, $X_3$, $X_4$, and $X_5$ is F.

This invention relates to cyclosporins of formula I

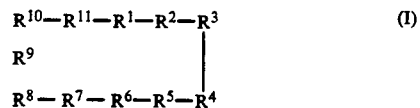

or pharmaceutically acceptable salts thereof wherein:

$R^1$ is MeBmt or dihydroMeBmt or defined according to formula III

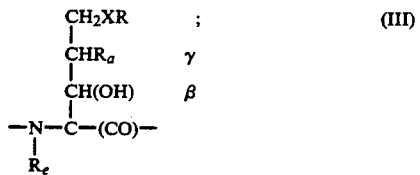

wherein:

X is S, SO, SO$_2$, O, N or C$_{1-6}$alkyl-N-;

$R_a$ is C$_{1-6}$alkyl;

$R_e$ is C$_{1-6}$alkyl or C$_{1-6}$alkylphenyl;

R is
- (a) hydrogen;
- (b) C$_{1-6}$alkyl or C$_{3-6}$cycloalkyl;
- (c) C$_{2-6}$alkenyl,
- (d) halo C$_{1-6}$alkyl;
- (e) phenyl;
- (f) C$_{1-6}$alkoxy C$_{1-6}$alkyl;
- (g) oxy C$_{1-6}$alkyl;
- (h) thio C$_{1-6}$alkyl;
- (i) C$_{1-6}$alkylthio C$_{1-6}$alkyl;
- (j) pyridyl, pyrryl, furyl or thienyl;
- (k) substituted phenyl, pyridyl, pyrryl, furyl or thienyl wherein the substitutent is
  - (1) hydroxyl;

(2) nitro;
(3) halo;
(4) cyano;
(5) —OCH$_2$O—;
(6) hydroxyl C$_{1-3}$alkyl;
(7) C$_{1-6}$alkyl or halo C$_{1-6}$alkyl;

(8) 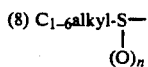

where n is 0, 1 or 2;
(9) formyl or C$_{1-6}$alkylcarbonyl;
(10) formylthio or C$_{1-6}$alkylcarbonylthio;
(11) C$_{1-6}$alkoxy;
(12) —NR$_b$COR$_c$ wherein R$_b$ and R$_c$ are independently H or C$_{1-6}$alkyl;
(13) NR$_b$R$_c$;
(14) NR$_b$CONR$_b$R$_c$;

R$^2$ is an amino acid residue selected from the group consisting of the residues of Abu, Ala, Nva, Ser, Thr, and Val or a fluorinated analog thereof;
R$^3$ is Sar; N-methyl-D-alanyl;
R$^4$ is MeLeu, MeVal or a fluorinated analog thereof;
R$^5$ is Val or Nva or a fluorinated analog thereof;
R$^6$ is MeLeu, MeVal, or a fluorinated analog thereof;
R$^7$ is Ala, Abu, or L-phenylalanyl or a fluorinated analog thereof;
R$^8$ is D-alanyl;
R$^9$ is MeLeu, MeVal, or a fluorinated analog thereof;
R$^{10}$ is MeLeu, MeVal, or a fluorinated analog thereof; and
R$^{11}$ is MeVal, MeNva or a fluorinated analog thereof;
with the proviso that at least one of R$^2$, R$^4$ to R$^7$, and R$^9$ to R$^{11}$ is a fluorinated analog of an amino acid.

In a first embodiment this invention relates to cyclosporins of formula I

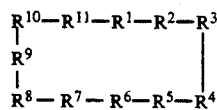 (I)

wherein:
R$^1$ is MeBMT, or dihydro-MeBMT;
R$^2$ is an amino acid residue selected from the group consisting of the residues of Abu, Ala Nva, Ser, Thr, and Val, or a fluorinated analog thereof, wherein a fluorinated analog represents the amino acid residue in which one or more of the various C—H bonds in the side chain are replaced with C—F bonds; for example, fluorinated analog of Abu represents

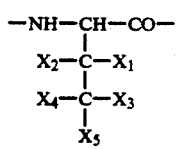

wherein X$_1$-X$_5$ independently is H or F with the proviso that at least one of X$_1$, X$_2$, X$_3$, X$_4$, and X$_5$ is F;
R$^3$ is Sar or D-MeAla;
R$^4$, R$^6$, R$^9$, and R$^{10}$ are MeLeu or a fluorinated analog thereof;
R$^5$ is Val or a fluorinated analog thereof;
R$^7$ is Ala or a fluorinated analog thereof;

R$^8$ is D-Ala; and
R$^{11}$ is MeVal or a fluorinated analog thereof; with the proviso that at least one of R$^2$, R$^4$ to R$^7$, and R$^9$ to R$^{11}$ is a fluorinated analog of an amino acid.

Preferably, this invention relates to a cyclosporin analog of formula I wherein:
R$^2$ is
(a) a fluorinated analog of L-alanine;
(b) a fluorinated analog of L-α-aminobutyric acid;
(c) a fluorinated analog of L-norvaline;
(d) a fluorinated analog of L-valine; or
(e) L-α-aminobutyric acid, L-norvaline, or L-threonine;
R$^5$ is valine or a fluorinated analog of valine; and
R$^{11}$ is N-methyl-valine or a fluorinated analog of N-methyl-valine;
with the proviso that at least one of R$^2$, R$^4$ to R$^7$, and R$^9$ to R$^{11}$ is a fluorinated analog of an amino acid.

In a even more preferred in this embodiment:
R$^2$ is
(a) 4,4-difluoro-Abu;
(b) 4-fluoro-Abu;
(c) 5-fluoro-Nva;
(d) 4-fluoro-Nva;
(e) 4-fluoro-Val;
(g) Abu;
(h) Nva; or
(i) Thr;
R$^5$ is Val or 4-fluoro-Val or the corresponding C-3 diastereoisomer; and
R$^{11}$ is MeVal or 4-fluoro-MeVal or the corresponding C-3 diastereoisomer;
with the proviso that at least one of R$^2$, R$^4$ to R$^7$, and R$^9$ to R$^{11}$ is a fluorinated analog of an amino acid.

Exemplifying the first embodiment of the invention are the compounds of the formula (I) which are:
(a) R$^1$ is MeBmt, R$^2$ is Abu, R$^3$ is Sar, R$^4$ is MeLeu, R$^5$ is 4-fluoro-Val, R$^6$ is MeLeu, R$^7$ is Ala, R$^8$ is D-Ala, R$^9$ is MeLeu, R$^{10}$ is MeLeu, R$^{11}$ is MeVal;
(b) R$^1$ is dihydroMeBmt, R$^2$ is Abu, R$^3$ is Sar, R$^4$ is MeLeu, R$^5$ is 4-fluoro-Val, R$^6$ is MeLeu, R$^7$ is Ala, R$^8$ is D-Ala, R$^9$ is MeLeu, R$^{10}$ is MeLeu, R$^{11}$ is MeVal;
(c) R$^1$ is MeBmt, R$^2$ is 4,4-difluoro Abu, R$^3$ is Sar, R$^4$ is MeLeu, R$^5$ is Val, R$^6$ is MeLeu, R$^7$ is Ala, R$^8$ is D-Ala, R$^9$ is MeLeu, R$^{10}$ is MeLeu, R$^{11}$ is MeVal; or
(d) R$^1$ is MeBmt, R$^2$ is Abu, R$^3$ is Sar, R$^4$ is MeLeu, R$^5$ is Val, R$^6$ is MeLeu, R$^7$ is Ala, R$^8$ is D-Ala, R$^9$ is MeLeu, R$^{10}$ is MeLeu, R$^{11}$ is 4-fluoro-MeVal
or pharmaceutically acceptable salts thereof.

A second embodiment of this invention is the compounds of formula I wherein:
R$^1$ is formula III wherein X, R, R$_a$ and R$_e$ are defined as above, wherein the stereochemistry at Center β is R; and at Center γ is S;
R$^2$ is Abu, Ala, Nva, Ser, Thr, Val; or a fluorinated analog thereof, and
R$^5$ is Val or Nva or a fluorinated analog thereof;
R$^{11}$ is MeVal, MeNva or a fluorinated analog thereof.
with the proviso that at least one of R$^2$, R$^5$, and R$^{11}$ is a fluorinated analog of an amino acid.

A class of compounds within the second embodiment of the invention is compounds of formula I wherein:
R$_a$ and Re are CH$_3$; and
X is S or O; and
R is
(a) hydrogen;
(b) C$_{1-6}$ alkyl;

(c) —CF$_3$;
(d) phenyl;
(e) —CH$_2$R$_b$ or —CH$_2$OC$_{1-6}$ alkyl; or
(f) —CH$_2$SH or —CH$_2$SC$_{1-6}$alkyl.

A subclass of the second embodiment is compounds of formula I wherein:
X is S; and
R is C$_{1-6}$alkyl or phenyl.
Exemplifying the second embodiment of the invention is compounds of formula I wherein:
(a) R$^1$ is (4S)-N,4-dimethyl-4-(methylthiomethyl)-L-threonyl, R$^2$ is Abu, R$^3$ is Sar, R$^4$ is MeLeu, R$^5$ is 4-fluoro-Val, R$^6$ is MeLeu, R$^7$ is Ala, R$^8$ is D-Ala, R$^9$ is MeLeu, R$^{10}$ is MeLeu, R$^{11}$ is MeVal;
(b) R$^1$ is (4S)-N,4-dimethyl-4-(ethylthiomethyl)-L-threonyl, R$^2$ is Abu, R$^3$ is Sar, R$^4$ is MeLeu, R$^5$ is 4-fluoro-Val, R$^6$ is MeLeu, R$^7$ is Ala, R$^8$ is D-Ala, R$^9$ is MeLeu, R$^{10}$ is MeLeu, R$^{11}$ is MeVal;
(c) R$^1$ is (4S)-N,4-dimethyl-4-(isopropylthiomethyl)-L-threonyl, R$^2$ is Abu, R$^3$ is Sar, R$^4$ is MeLeu, R$^5$ is 4-fluoro-Val, R$^6$ is MeLeu, R$^7$ is Ala, R$^8$ is D-Ala, R$^9$ is MeLeu, R$^{10}$ is MeLeu, R$^{11}$ is MeVal;
(d) R$^1$ is (4S)-N,4-dimethyl-4-(methylthiomethyl)-L-threonyl, R$^2$ is Abu, R$^3$ is Sar, R$^4$ is MeLeu, R$^5$ is Val, R$^6$ is MeLeu, R$^7$ is Ala, R$^8$ is D-Ala, R$^9$ is MeLeu, R$^{10}$ is MeLeu, R$^{11}$ is 4-fluoro-MeVal;
(e) R$^1$ is (4S)-N,4-dimethyl-4-(ethylthiomethyl)-L-threonyl, R$^2$ is Abu, R$^3$ is Sar, R$^4$ is MeLeu, R$^5$ is Val, R$^6$ is MeLeu, R$^7$ is Ala, R$^8$ is D-Ala, R$^9$ is MeLeu, R$^{10}$ is MeLeu, R$^{11}$ is 4-fluoro-MeVal; or
(f) R$^1$ is (4S)-N,4-dimethyl-4-(isopropylthiomethyl)-L-threonyl, R$^2$ is Abu, R$^3$ is Sar, R$^4$ is MeLeu, R$^5$ is Val, R$^6$ is MeLeu, R$^7$ is Ala, R$^8$ is D-Ala, R$^9$ is MeLeu, R$^{10}$ is MeLeu, R$^{11}$ is 4-fluoro-MeVal;
or pharmaceutically acceptable salts thereof.

The invention further encompasses novel fluorinated amino acids, one or more of which may be incorporated in the fluorinated cyclosporins of the invention. These novel fluorinated amino acids are selected from a group consisting of
(a) 4,4-difluoro-L-α-aminobutyric acid;
(b) 4-fluoro-L-valine;
(c) 4-fluoro-L-methyl-valine;
(d) 4-fluoro-L-norvaline;
(e) 5-fluoro-L-norvaline; and
(f) 4-fluoro-L-α-aminobutyric acid.

Compounds of the present invention are conveniently prepared using the procedures described generally below and more explicitly in the Example Section thereafter.

Preparation of the cyclosporins of this invention are depicted in Scheme I below.

Preparation of the "C-9 threonine derivatives" is depicted in scheme II. Details of the preparation of "C-9 threonine derivatives" and their incorporation into cyclosporin analogs is disclosed in the U.S. application Ser. No. 057,196 filed by B. E. Witzel on Jun. 3, 1987 (now U.S. Pat. No. 4,798,823) which is hereby incorporated by reference.

Synthesis of the fluorinated amino acids employed in synthesis of the cyclosporins is accomplished by the general method of photo-fluorination (See J. Kollonitsch, Isr. J. Chem., 17, 51–59, 1978, and reference therein.) For example, photofluorination of L-α-aminobutyric acid gives 4,4-difluoro-L-α-aminobutyric acid. Photofluorination of L-valine gives 4-fluoro-3(S)-L-valine and 4-fluoro-3(R)-L-valine. Photofluorination of L-norvaline gives 4-fluoro-4(S)-L-norvaline, 4-fluoro-4(R)-L-norvaline and 5-fluoro-L-norvaline.

The remaining starting materials for the process are available commercially, and/or their method of preparation is known.

Now turning to Scheme I, the cyclosporins of this invention are conveniently prepared via step-wise linking and cyclization of linear undecapeptides according to well-established procedures, modified slightly for better results. (See R. M. Wenger et al. in Helv. Chim. Acta, 67, 502(1984) ). While in Scheme I, a fluorinated amino acid analog is incorporated at position 2, the procedure as outlined here and exemplified, hereinafter, may be used to incorporate a fluorinated amino acid analog at any of the positions R$^2$, and R$^4$ to R$^7$ and R$^9$ to R$^{11}$. Similarly, a fluorinated amino acid analog may be incorporated at more than one of the positions R$^2$, R$^4$ to R$^7$ and R$^9$ to R$^{11}$.

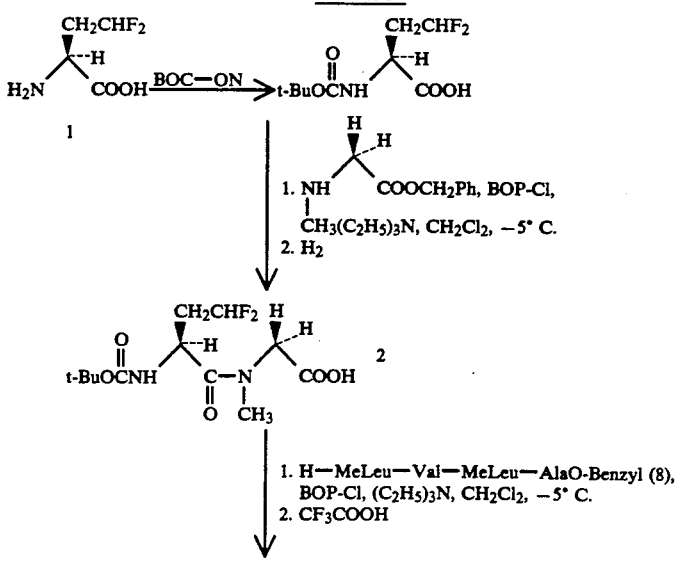

Scheme I

Scheme I

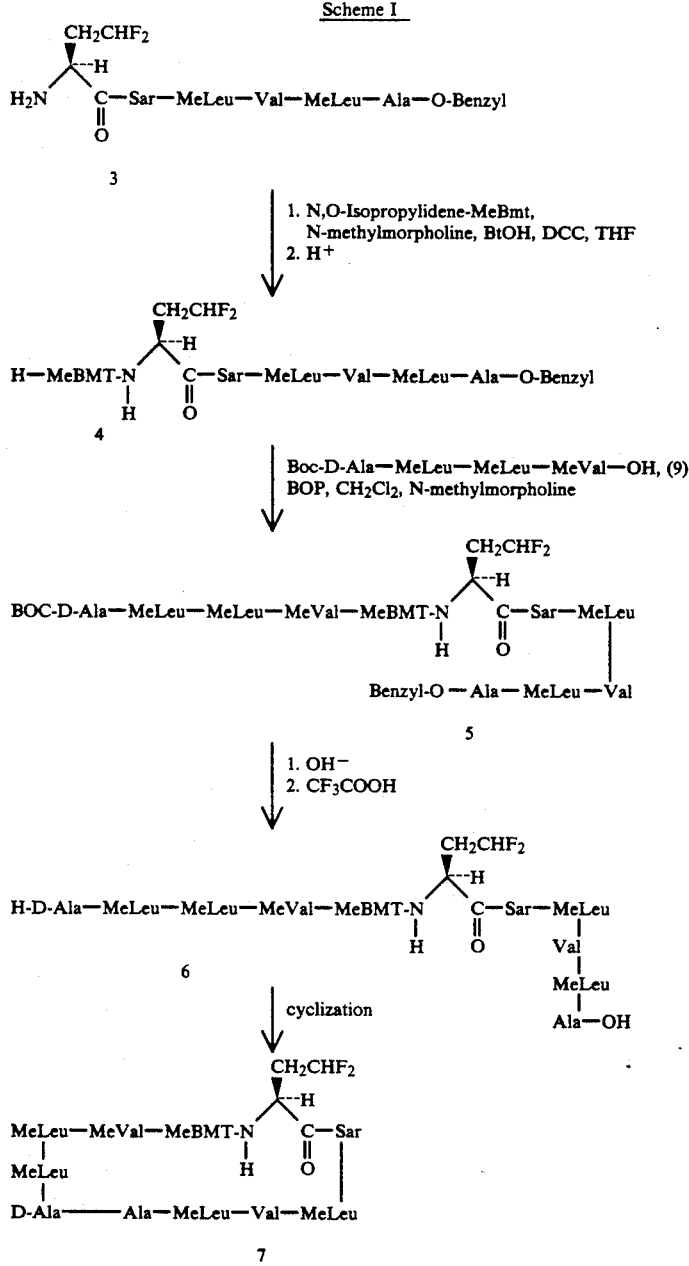

According to Scheme I, a fluorinated amino acid such as 1 is N-protected as its BOC derivative, then coupled with a position-3 amino acid, such as sarcosine benzyl ester, in the presence a peptide coupling reagent, such as bis-(2-oxo-3-oxazolidinyl)phosphinic chloride (BOP-Cl) to afford after hydrogenolysis the O-deprotected dipeptide 2. Dipeptide 2 is then coupled with fluorinated or non-fluorinated amino acids $R_4$ to $R_7$ one at a time or when convenient with the known H-MeLeu-Val-MeLeu-Ala-O-Benzyl tetrapeptide (See R. M. Wenger, Helv. Chim. Acta. 67 (1984) 502) with a coupling reagent such as BOP-Cl as to afford, after N-deprotection with trifluoroacetic acid or similar reagent, the hexapeptide 3.

Heptapeptide 4 is then formed by first coupling with N,O-isopropylidene-MeBMT in the presence of N-hydroxy-benzotriazole and 1,3-dicyclohexylcarbodiimide, and subsequent removal of the isopropylidene acetal group by treatment with an acid, for example, HCl in methanol. As elaborated in the U.S. application Ser. No. 057,196 filed by B. E. Witzel on Jun. 3, 1987 (now U.S. Pat. No. 4,798,823) sulfur containing "C-9" amino acids may be incorporated by essentially the same procedure. The protected linear undecapeptide 5 is prepared by condensation of 4 with the known Boc-D-Ala-MeLeu-MeLeu-MeValOH tetrapeptide [R. M. Wenger, Helv. Chim. Acta. 66 (1983) 2672] in the presence of benzotriazol-1-yloxytris(dimethylamino)phosphonium hexafluorophosphate (BOP reagent). O-deprotection is achieved by treatment with aqueous NaOH in ethanol and N-deprotection by treatment with trifluoroacetic acid. The linear unprotected undecapeptide 6 is then cyclized at high dilution in the presence of a peptide coupling reagent, such as 1-propanephosphonic acid cyclic anhydride in the presence of 4-dimethylaminopyridine, to afford (4,4-difluoro-Abu)-cyclosporin A (7).

The dihydro MeBMT derivatives of the fluorinated cyclosporin analogs are prepared by hydrogenation in an alcohol, such as methanol or ethanol, in the presence of a catalyst, such as 10% palladium-on-charcoal.

Treatment of the fluorinated cyclosporin analogs containing a sulfur atom in place of the carbon-carbon double bond in the MeBMT residue with an oxidant, such as sodium metaperiodate or m-chloroperbenzoic acid, affords the corresponding sulfoxide or sulfone.

Table I below lists the representative compounds prepared by following essentially the same procedures described in Scheme I, but employing the appropriate tetrapeptide, substituted with a fluorinated amino acid.

TABLE I

Representative Compounds

```
MeLeu——R11——R1—R2—Sar
  |                    |
MeLeu                MeLeu
  |                  /
D-Ala—Ala—MeLeu—R5
```

| Compound | $R^1$ | $R^2$ | $R^5$ | $R^{11}$ | FAB-MS$^a$ (Molecular Ion) |
|---|---|---|---|---|---|
| (1) | MeBMT | 4,4-difluoro-Abu | Val | MeVal | 1238 |
| (2) | dihydroMeBMt | 4,4-difluoro-Abu | Val | MeVal | 1240 |
| (3) | MeBMT | 4-fluoro-Abu | Val | MeVal | 1220 |
| (4) | MeBMT | 4-fluoro-Nva | Val | MeVal | 1234 |
| (5) | MeBMT | 5-fluoro-Nva | Val | MeVal | 1234 |
| (6) | MeBMT | Abu | 4-fluoroVal | MeVal | 1220 |
| (7) | dihydroMeBMT | Abu | 4-fluoroVal | MeVal | 1222 |
| (8) | MeBMT | Abu | Val | 4-fluoro-MeVal | 1220 |
| (9) | DMT$^b$ | Abu | 4-fluoroVal | MeVal | 1226 |

$^a$Fast Atom Bombardment Mass spectroscopy
$^b$(4S)-N,4-dimethyl-4-(methylthiomethyl)-L-threonyl The key "C-9" threonine derivatives of formula III are prepared according to the method described in U.S. application Ser. No. 057,196 filed by Witzel on Jun. 3, 1987 (now U.S. Pat. No. 4,798,823).

Scheme II illustrates the preparation of the "C-9" threonine according to the procedure described.

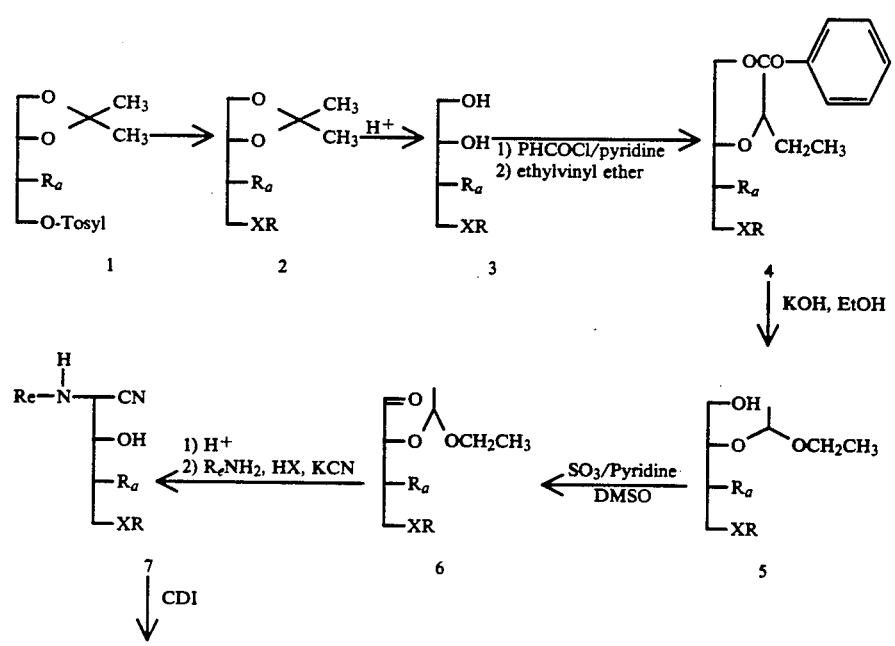

Scheme II

Scheme II -continued

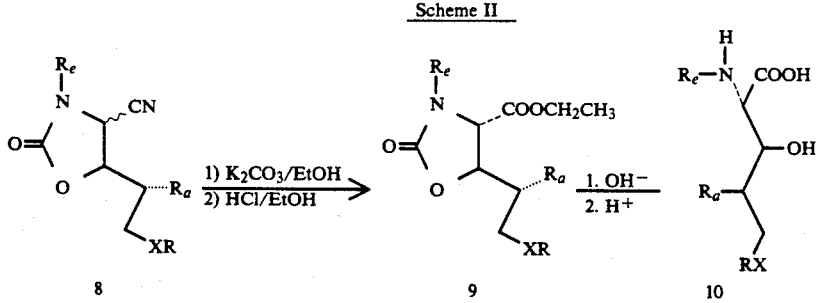

The groups "$R_a$" and "$R_e$" depicted in Scheme II are defined identically with "$R_a$" and "$R_e$", respectively according to the broadest description provided in the Detailed Description of the invention. In Scheme II, compound 1 is prepared from diethyl L(+)-tartrate according to the procedure of R. M. Wenger, *Helv. Chim. Acta*, 66. 2317 (1983) or Kenji Mori et al., *Tetrahedron*, 36, 87 (1980). Compound 2 is prepared by displacement of the tosylate with a nucleophile such as a sodium mercaptide. Compound 3 is prepared by addition of a dilute mineral acid to a solution of compound 2 in peroxide-free tetrahydrofuran. Protection of the hydroxyl group at position-1 as its benzoate ester and further reaction with ethylvinylether results in compound 4. Compound 5 is prepared by addition of 10N KOH or NaOH to crude compound 4 in a cold ethanol. To a solution of compound 5 is dried DMSO is added triethylamine follow by dropwise addition of sulfur trioxide pyridine complex in dry DMSO resulting in compound 6. After treatment with 1N mineral acid, such as hydrochloric acid, the compound is dissolved in methanol and treated sequentially with potassium cyanide, $R_eNH_2$, and HX resulting in compound 7. Subsequent addition of 1,1'-carbonyldiimidazole results in compound 8. Compound 8 is reacted with anhydrous potassium carbonate. To a solution of the resulting product in 95% ethanol is added 1N HCl resulting in compound 9. Addition of a strong base, such a potassium hydroxide or sodium hydroxide, followed by acidification results in compound 10.

This invention also relates to a method of treatment for patients suffering from immunoregulatory abnormalities involving the administration of a compound of formula I as the active constituent.

For the treatment of these conditions and diseases caused by immunoirregularity, a compound of formula I may be administered orally, topically, parenterally, by inhalation spray or rectally in dosage unit formulations containing conventional non-toxic pharmaceutically acceptable carriers, adjuvants and vehicles. The term parenteral, as used herein, includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

Dosage levels of the order from about 0.5 mg to about 50 mg per kilogram of body weight per day are useful in the treatment of the above-indicated conditions (from about 25 mg to about 2.5 gms. per patient per day).

The amount of active ingredient that may be combined with the carrier materials to produce a single dosage form will vary depending upon the host treated and the particular mode of administration. For example, a formulation intended for the oral administration of humans may contain from 5 mg to 2.5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of formula I have immunosuppressive activities and are thereby useful in the treatment of various "autoimmune" and chronic inflammatory diseases. They may also be useful in the prevention of graft rejection or rejection of "donor" organs in transplantation operations. Table 2 illustrates the pharmacological activity of representative compounds of the present invention.

TABLE 2

IMMUNOSUPPRESSIVE ACTIVITIES OF FLUORINATED CYCLOSPORIN ANALOGS $$\text{MeLeu—R}^{11}\text{——R}^{1}\text{—Abu—Sar}$$
$$\text{MeLeu} \qquad \text{MeLeu}$$
$$\text{D-Ala—Ala—MeLeu—R}_5$$

| $R^1$ | $R^{11}$ | $R^5$ | Cyclophilin Binding[a,b] | T-Cell Proliferation Inhibition[b,c] |
|---|---|---|---|---|
| MeBMT | MeVal | 4-fluoro-Val | 232 | 144 |
| dihydroMeBMT | MeVal | 4-fluoro-Val | 239 | 163 |
| MeBMT | 4-fluoro-MeVal | Val | 69 | 47 |
| DMT[d] | MeVal | 4-fluoro-Val | 240 | 10 |

[a]This assay is described in detail by R. Handschumacher et al., Science, 226 (1984) 544.
[b]The data are expressed as % CsA's activity (CsA(cyclosproin A) = 100).
[c]T-Cell Roliferation Assay:
[d](4S)-N,4-dimethyl-4-(methylthiomethyl)-L-threonyl T-cell proliferation was measured in mouse T-cell cultures stimulated with ionomycin plus phorbol myristate acetate (PMA). Spleen cell suspensions from C57B1/6 mice were prepared and separated on nylon wool columns. The recovered T-cells were suspended at $10^6$ cells /ml in complete culture medium with addition of ionomycin (250 ng/ml) and PMA (10 ng/ml). The cell suspension was immediately distributed in 96 well-flat bottom microculture plates at 100 μl/well. Control medium or various concentrations of test compound were added in triplicate wells at 10 μl/well. The plates were incubated at 37° C. in a humidified atmosphere of 5% $CO_2$-95% air for 44 hours. At 44 hours of culture, the plates received 20 μl/well of a solution of (3-(4,5-dimethylthiazol-2-yl)-2,5-diphenyltetrazolium bromide (MMT) in PBS (10 mg/ml). To dissolve the purple crystals of MTT formazan produced by metabolically active cells, 100 μl of a 10% SDS-0.01 N hydrochloric acid solution was added to each well. The culture plates were incubated at 37° C. in a 5% CO₂ incubator. The plates were read at 570-600 nm in a multiwell scanning spectrophotometer. The absorbance (specific OD) of experimental wells was corrected for that of wells with unstimulated cells or no cells. The percent inhibition of proliferation was calculated according to the formula:

$$\% \text{ Inhib.} = 100 - \frac{\text{Specific } OD \text{ experimental}}{\text{Specific } OD \text{ control medium}} \times 100$$

The following examples illustrate the preparation of the invention compounds of formula I and as such are not to be considered as limiting the invention set forth in the claims appended thereto:

EXAMPLE 1

Cyclo[-((2S,3R,4R,6E)-3-hydroxy-4-methyl-2-methylamino-6-octenoyl)-L-2-aminobutyryl-sarcosyl-N-methyl-L-Leucyl-4-fluoro-valyl-N-methyl-L-leucyl-L-alanyl-D-alanyl-N-methyl-L-Leucyl-N-methyl-L-leucyl-N-methyl-L-valyl]

Step 1: Boc-4-fluoro-3-(R,S)-L-valine

To a suspension of 990 mg (0.0073 mole) of (R,S)-4-fluoro-(L)-valine in 10 ml of dioxane and 10 ml of water was added 1.12 g (0.0111 mole) of triethylamine. 2.12 g (0.0086 mole) of BOC-ON was added and stirred at room temperature for 16 hours. The reaction was diluted with 40 ml of water and 60 ml of ether. The aqueous layer was separated and made acid with 2.5N hydrochloric acid, then extracted with 3×40 ml of ethyl acetate. The organic layers were dried over magnesium sulfate and evaporated leaving the crude product as a thick oil. This was reacted in step 2 without further purification. The crude yield is 94% of theory. Fast atom bombardment mass spectroscopy (FAB m.s.) showed a molecular ion peak at 236.

Step 2: BOC-4-fluoro-3(R,S)-L-Valyl-N-Methyl-Leucyl-L-Alanine benzyl ester

A solution of 1.6 g (0.0069 mole) of Boc-4-fluoro-3(R,S)-L-valine and 2.11 g (0.0069 mole) of N-methyl-L-leucyl-L-alanine benzyl ester (R. M. Wenger, Helv. Chim. Acta 67 (1984)502) in 70 ml of dry methylene chloride was stirred and cooled at −10° C. After 15 minutes, 1.69 g. (0.0167 mole) of dry triethylamine was added. The reaction was stirred for 5 minutes and 1.93 g (0.0076 mole) of N,N-bis(2-oxo-3-oxazolidinyl)phosphorodiamidic chloride was added. The reaction mixture was stirred at −10° C. for 16 hours, then evaporated to a small volume. The residue was taken up between 150 ml of ether and 50 ml of 10% potassium bisulfate. The ether layer was separated, washed with 3×35 ml of saturated sodium bicarbonate, dried over magnesium sulfate, and evaporated. The residue was chromatographed on silica gel with 1:1 ether-hexane as the eluent. The title compound was obtained as a mixture of diastereoisomers and weighed 1.79 g. The yield was 50% of theory and FAB m.s. showed a molecular ion peaks at 524.

Step 3: 4-fluoro-3(R,S)-L-Valyl-N-Methyl-L-Leucyl-L-alanine benzyl ester

A solution of 1.75 g (0.0033 mole) of Boc-4-fluoro-3(R,S)-L-Valyl-N-Methyl-L-Leucyl-L-Alanine benzyl ester in 17 ml of dry methylene chloride was stirred and cooled at −10° C. as 17 ml of trifluoroacetic acid, which was previously cooled at the same temperature, was added. The reaction was stirred and kept at −5° C. for 16 hours, then poured carefully with stirring into a mixture of 21 g of sodium bicarbonate, ice, and 100 ml of methylene chloride. After 5 minutes the organic layer was separated and washed with 3×30 ml of saturated sodium bicarbonate solution. The methylene chloride layer was dried over magnesium sulfate, and evaporated in vacuo to give 1.38 g of a stiff oil as the product. The yield was 99% of theory and the FAB m.s. showed a molecular ion peak at 424.

Step 4: Box-N-Methyl-L-leucyl-4-fluoro-3(R,S)-L-Valyl-N-Methyl-L-Leucyl-L-Alanine benzyl ester A solution of 1.46 g (0.0059 mole) of Boc-N-methyl-L-leucine in 90 ml of dry methylene chloride was stirred and cooled at 0° C. while one-half of 1.68 g. (0.0130 mole) of diisopropylethylamine was added, followed by 1.65 g. (0.0065 mole) of N,N-bis(2-oxo-3-oxazolidinyl)phosphorodiamidic chloride. The reaction was stirred at 0° C. for 4 hours. The remaining diisopropylethylamine was added and a solution of 4-fluoro-3(R,S)-L-Valyl-N-Methyl-L-leucyl-L-alanine benzyl ester in 15 ml of dry methylene chloride. This was stirred and kept at 0° C. for 20 hours. The reaction mixture was diluted with 50 ml of methylene chloride, extracted with 35 ml of 5% potassium bisulfate solution, and washed with 2×30 ml of saturated sodium bicarbonate solution. The organic layer was dried over magnesium sulfate and chromatographed on silica gel using 2:1 ether-hexane as the eluent. The faster moving diastereoisomer was obtained as the major component and weighed 700 mg. This was reacted further in step 5. The yield was 33% of theory and FAB m.s. shows a molecular ion peak at 651.

Step 5: N-methyl-L-leucyl-4-fluoro-L-valyl-N-methyl-L-leucyl-L-alanine benzyl ester To a stirred solution of 650 mg (0.001 mole) of Boc-N-methyl-L-leucyl-4-fluoro-L-valyl-N-methyl-L-leucyl-L-alanine benzyl ester in 10 ml of dry methylene chloride and cooled at 10° C. was added 6.5 ml of trifluoroacetic acid, which was previously cooled at −15° C. The reaction was stirred for 16 hours, then carefully poured into a mixture of 7.7 g. of sodium bicarbonate, ice, and 75 ml of methylene chloride with stirring. The organic layer was extracted with 3×20 ml of saturated sodium bicarbonate solution, then dried over magnesium sulfate. The solvent was removed in vacuo leaving the product as a stiff oil, which weighed 540 mg. The yield is 989% of theory and the FAB m.s. showed a molecular ion peak at 551.

Step 6: Boc-L-2-aminobutyryl-Sarcosyl-N-methyl-L-Leucyl-4-fluoro-L-valyl-N-methyl-L-leucyl-L-alanine benzyl ester A solution of 274 mg (0.00010 mole) of Boc-L-2-aminobutyryl-sarcosine (R. M. Wenger, Helv. Chim. Acta, 67 (1984)502) and 500 mg (0.009 mole) of N-methyl-L-leucyl-4-fluoro-valyl-N-methyl-L-leucyl-alanine benzyl ester in 40 ml of dry methylene chloride was stirred and cooled at −5° C. 245 mg of dry triethylamine was added. After 10 minutes 280 mg (0.0011 mole) of N,N-bis(3-oxo-3-oxazolidinyl) phosphordiamidic chloride was added and the reaction was stirred and cooled at −10° C. for 16 hours. The reaction mixture was concentrated to a small volume and placed on a column of silica gel. The column was first eluted with ether, then with 5% ethyl acetate in ether giving 613 mg of the product as a thick oil. The yield is 84% of theory and FAB m.s. showed a molecular ion peak at 807.

Step 7: L-2-aminobutyryl-sarcosyl-N-methyl-L-leucyl-4-fluoro-L-valyl-N-methyl-L-leucyl-L-alanine benzyl ester A solution of 550 mg (0.0007 mole) of Boc-L-2-aminobutyryl-sarcosyl-N-methyl-L-leucyl-4-fluoro-L-valyl-N-methyl-L-leucyl-L-alanine benzyl ester in 5.5 ml of dry methylene chloride was stirred and cooled at −10° C., as 5.5 ml of trifluoroacetic acid cooled at −15° C. was added. The reaction was stirred and cooled at −5° C. for 16 hours, then poured carefully into a mixture of 6 g. of sodium bicarbonate, ice, and 100 ml of methylene chloride. After stirring for 10 minutes the organic layer was separated and washed with 3×25 ml of saturated sodium bicarbonate solution. The organic layer was dried over magnesium sulfate and evaporated in vacuo giving 470 mg. of product as a glass. The yield is 95% of theory, and FAB showed m.s. a molecular ion peaks at 707.

Step 8: ((4S,5R,1'R,3'E)-2,2,3-trimethyl-5-(1'-methyl-3'-pentenyl)-4-oxazolidinecarbonyl)-L-2-aminobutyryl-sarcosyl-N-methyl-L-leucyl-4-fluoro-L-valyl-N-methyl-L-leucyl-L-alanine benzyl ester To a mixture of (4S,5R,1'R,3'E)-2,2,3-trimethyl-5-(1'-methyl-3'-pentenyl)-4-oxazolidinecarboxylic acid (prepared by heating at reflux temperature a solution of (2S, 3R, 4R, 6E)-3-hydroxy-4-methyl-2-methylamino-6-octenoic acid [prepared by the process set forth in R. M. Wenger, Helv. Chim. Acta, 66 (1983) 2308] (129 mg., 0.64 mmol.) in dry acetone (60 ml.) for 48 hours and subsequent evaporation under diminished pressure) in approximately 0.3 ml. acetone were added, successively with stirring under a nitrogen atmosphere, dry tetrahydrofuran (6.5 ml.), N-methylmorpholine (81 μl., 0.74 mmol.), hydroxybenzotriazole (175 mg., 1.30 mmol.), and a solution of L-2-aminobutyryl-sarcosyl-N-methyl-L-leucyl-4-fluoro-L-valyl-N-methyyl-L-leucyl-L-alanine benzyl ester (465 mg., 0.658 mmol.) in dry tetrahydrofuran (4 ml.). The reaction mixture was cooled in an ice bath and 1,3-dicyclohexylcarbodiimide (139 mg., 0.67 mmol.) added. The mixture was allowed to attain room temperature, and stirring was continued for an additional 24 hours. The mixture was then diluted with dichloromethane (30 ml.) and washed with saturated sodium hydrogencarbonate solution (20 ml.). The aqueous layer was extracted with dichloromethane (20 ml.), and the combined organic extracts were dried (sodium sulfate) and evaporated. The residue was triturated with diethyl ether, filtered, and evaporated. The resulting crude material was applied to a column of silica gel (Merck #7734, packed as a slurry in 2% methanol in dichloromethane). Elution was effected with 2% methanol in dichloromethane. Fractions containing pure product were combined and evaporated to afford the protected N,O-isopropylidene-MeBmt-Abu-Sar-MeLeu-4-Fluoro-Val-MeLeu-AlaOBzl heptapeptide as a thick syrup; yield 381 mg. (64%). Its 200 MHz NMR spectrum in chloroform-d was in accord with the desired structure.

Step 9: ((2S,3R,4R,6E)-3-hydroxy-4-methyl-2-methyl-amino-6-octenoyl)-L-2-aminobutyryl-sarcosyl-N-methyl-L-leucyl-4-fluoro-L-valyl-N-methyl-L-leucyl-L-alanine benzyl ester To a solution of N,O-isopropylidene-MeBmt-Abu-Sar-MeLeu-4-Fluoro-Val-MeLeu-AlaOBzl (381 mg., 0.41 mmol.) in methanol (6 ml.) was added with stirring 1N hydrochloric acid (0.44 ml.). The reaction mixture was stirred for 18 hours at room temperature, then neutralized with solid sodium hydrogencarbonate (250 mg.). The mixture was filtered, the filter washed with methanol, and the combined filtrate and washings evaporated. The crude material was taken up in dichloromethane and filtered. The resulting syrup was applied to a column of silica gel (Merck #7734, packed as a slurry in 4% methanol in dichloromethane). Elution was effected with 4% methanol in dichloromethane. Fractions containing slower-moving product were combined and evaporated to afford the partially deprotected H-MeBmt-Abu-Sar-MeLeu-4-Fluoro-Val-MeLeu-AlaOBzl heptapeptide as a thick syrup: yield 257 mg. (70.5%).

Step 10: Boc-D-Alanyl-N-methyl-L-leucyl-N-methyl-L-leucyl-N-methyl-L-valyl-((2S,3R,4R,6E)-3-hydroxy-4-methyl-2-methylamino-6-octenoyl)-L-2-aminobutyryl-sarcosyl-N-methyl-L-leucyl-4-fluoro-L-valyl-N-methyl-L-leucyl-L-alanine benzyl ester To a solution of Boc-D-Ala-MeLeu-MeLeu-MeValOH (prepared by the process set forth in R. M. Wenger, Helv. Chim. Acta. 66 (1983) 2672) (161 mg., 0.289 mmol.) and H-MeBmt-Abu-Sar-MeLeu-4-fluoro-ValMeLeu-AlaOBzl (257 mg., 0.289 mmol.) in dry dichloromethane (10 ml.) were added N-methylmorpholine (38 μl, 0.346 mmol.) and benzotriazol-1-yloxytris(-dimethylamino)phosphonium hexafluorophosphate (191 mg., 0.432 mmol). The reaction mixture was stirred 4 days at room temperature under a nitrogen atmosphere. It was then diluted with dichloromethane (100 ml.), washed with water (50 ml.), dried (sodium sulfate) and evaporated. The crude product was chromatographed on a column of silica gel (Merck #7734, packed as a slurry in 4% methanol in dichloromethane). Elution was effected with 4% methanol in dichloromethane. Fractions containing pure product were combined and evaporated to afford the desired Boc-D-Ala-MeLeu-MeLeu-MeVal-MeBmt-Abu-Sar-MeLeu-4-Fluoro-Val-MeLeu-AlaOBzl undecapeptide; yield 258 mg. (62.5%).

Step 11: Boc-D-Alanyl-N-methyl-L-leucyl-N-methyl-L-leucyl-N-methyl-L-valyl-((2S,3R,4R,6E)-3-hydroxy-4-methyl-2-methylamino-6-octenoyl)-L-2-aminobutyryl-sarcosyl-N-methyl-L-leucyl-4-fluoro-L-valyl-N-methyl-L-leucyl-L-alanine To a solution of Boc-D-Ala-MeLeu-MeLeu-MeVal-MeBmt-Abu-Sar-MeLeu-4-Fluoro-Val-MeLeu-AlaOBzl (258 mg., 0.181 mmol.) in ethanol (7 ml.) cooled to ice temperature was added 0.2N aqueous sodium hydroxide (0.9 ml.). The reaction mixture was kept at 5° C. for 24 hours, brought to about pH 0.5 with several drops of glacial acetic acid and then evaporated under diminished pressure. The residue was taken up in dichloromethane (25 ml.) and washed with water (12 ml.). The aqueous layer was extracted with dichloromethane, and the combined organic extracts were dried (sodium sulfate) and evaporated. The resulting material was applied to a column of silica gel (Merck #7734, packed as a slurry in 4% methanol in dichloromethane). Elution initially with 4% methanol in dichloromethane gave unreacted starting material and benzyl alcohol; subsequent elution with 15% methanol in dichloromethane afforded the partially protected Boc-D-Ala-MeLeu-MeLeu-MeVal-MeBmt-Abu-Sar-MeLeu-4-Fluoro-Val-MeLeu-AlaOH undecapeptide; yield 159 mg. (65.8%).

Step 12: D-Alanyl-N-methyl-L-leucyl-N-methyl-L-Leucyl-N-methyl-L-valyl-((2S,3R,4R,6E)-3-hydroxy-4-methyl-2-methylamino-6-octenoyl)-L-2-aminobutyryl-sarcosyl-N-methyl-L-leucyl-4-fluoro-L-valyl-N-methyl-L-leucyl-L-alanine Boc-D-Ala-MeLeu-MeLeu-MeVal-MeBmt-Abu-Sar-MeLeu-4-Fluoro-Val-MeLeu-AlaOH (159 mg., 0.12 mmol.) was cooled to −15° C. and treated with precooled trifluoroacetic acid (3 ml.) for 90 minutes at −15° C. The reaction mixture was then evaporated under diminished pressure (bath temperature of 0° C.) and co-evaporated several times with dichloromethane. The crude material was taken up in dichloromethane (25 ml.) and washed with saturated sodium hydrogencarbonate solution (12 ml.). The organic layer was dried (sodium sulfate) and evaporated. The product was triturated with diethyl ether and dried in vacuo; yield 119 mg. (81%).

Step 13: cyclo[-((2S,3R,4R,6E)-3-hydroxy-4-methyl-2-methylamino-6-octenoyl)-L-2-aminobutyrylsarcosyl-N-methyl-L-leucyl-4-fluoro-valyl-N-methyl-L-leucyl-alanyl-D-alanyl-N-methyl-L-leucyl-N-methyl-L-leucyl-N-methyl-L-valyl]

To a solution of H-D-Ala-MeLeu-MeLeu-MeVal-MeBmt-Abu-Sar-MeLeu-4-Fluoro-Val-MeLeu-AlaOH (119 mg., 0.096 mmol.) in dichloromethane (400 ml.) were added 4-dimethylaminopyridine (60 mg., 0.491 mmol.) followed by 1-propanephosphonic acid cyclic anhydride (50 wt. % solution in dichloromethane) (0.3 ml.). The reaction mixture was stirred at room temperature for 24 hours, concentrated to approximately 25 ml. and washed with saturated sodium hydrogencarbonate solution. The organic layer was dried (sodium sulfate) and evaporated. The crude material was applied to a column of silica gel (Merck #7734, packed as a slurry in 2:1 hexane-acetone). Elution was effected with 2:1 hexane-acetone. Fractions containing pure product were combined and evaporated to give 4-fluoro-Val[5] cyclosporin A as a white amorphous solid; yield 57 mg. (48.7%). Its 400 MHz NMR spectrum in chloroform-d was in accord with the desired structure. FAB m.s. showed a molecular ion at m/z 1220.

EXAMPLE 2

Cyclo[-((2S,3R,4S)-N-4-dimethyl-4-methylthiomethyl)-threonyl)-L-α-aminobutyryl-Sarcosyl-N-methyl-L-Leucyl-4-fluoro-Valyl-N-methyl-L-Leucyl-Alanyl-D-Alanyl-N-methyl-L-Leucyl-N-methyl-L-Leucyl-N-methyl-L-Valyl]

Follow step 1 through step 7 as in Example 1; thereafter proceed as follows:

Step 8: (4S,5R,1'S)-2,2,3-Trimethyl-5-(1-'(methylthiomethyl)-ethyl)-(4-oxazolidinecarbonyl)-L-α-aminobutyryl-sarcosyl-N-methyl-L-leucyl-4-fluoro-L-valyl-N-methyl-L-leucyl-L-alanine benzyl ester (2S,3R,4S)3-Hydroxy-4-methyl-2-(methylamino-5-(methylthio)-pentanoic acid (0.48 mmol.) is converted to its dimethyloxazolidine derivative via reaction with acetone as per Example 1, Step 8. This acid, containing approximately 0.5 ml of acetone, was then treated successively with stirring under a nitrogen atmosphere with 2 ml dry tetrahydrofuran, N-methylmorpholine (40 μl.,), N-hydroxy-benzotriazole (120 mg., 0.88 mmol.), and a solution of L-α-aminobutyryl-sarcosyl-N-methyl-L-leucyl-4-fluoro-L-valyl-N-methyl-L-leucyl-L-alanine benzyl ester (320 mg., 0.45 mmol.) in dry tetrahydrofuran (4 ml.). The reaction mixture was cooled in an ice bath and 1,3-dicyclohexylcarbodiimide (93 mg., 0.45 mmol.) added. The mixture was allowed to attain room temperature, and stirring was continued for an additional 24 hours. The mixture was then diluted with dichloromethane (30 ml.) and washed with saturated sodium hydrogen-carbonate solution (20 ml.). The aqueous layer was extracted with dichloromethane (20 ml.), and the combined organic extracts were dried (sodium sulfate) and evaporated. The residue was triturated with diethyl ether, filtered, and evaporated. The resulting crude material was applied to a column of silica gel (Merck #7734, packed as a slurry in 2% methanol in dichloromethane). Elution was effected with 2% methanol in dichloromethane. Fractions containing pure product were combined and evaporated to afford the protected N,O-isopropylideneDMT-Abu-Sar-MeLeu-4-Fluoro-Val-MeLeu-AlaOBzl hepta-peptide as a glaze. Its 200 MHz NMR spectrum in chloroform-d was in accord with the desired structure.

Step 9: (2S,3R,4S)3-Hydroxy-4-methyl-2-(methylamino-5-(methylthio)-pentanoyl-L-α-aminobutyrylsarcosyl-N-methyl-L-leucyl-4-fluoro-L-valyl-N-methyl-L-leucyl-L-alanine-benzyl ester To a solution of N,O-isopropylidene-DMT-Abu-Sar-MeLeu-4-Fluoro-Val-MeLeu-AlaOBzl (143 mg., 0.15 mmol.) in a mixture of methanol (4 ml.) and water (1 drop) was added with stirring 1N hydrochloric acid (0.20 ml.). The reaction mixture was stirred for 18 hours at room temperature, then neutralized with solid sodium hydrogencarbonate (25 mg.). The mixture was diluted with methylene chloride, treated with water (3 ml), separated the aqueous layer extracted one time with dichloromethane, the organic layer dried (Na$_2$SO$_4$) and concentrated to an oil. The product was used as is in the following step.

Step 10: Boc-D-Alanyl-N-methyl-L-leucyl-N-methyl-L-leucyl-N-methyl-L-valyl-(2S,3R,4S)3-Hydroxy-4-methyl-2-(methylamino-5-(methylthio)pentanoyl-L-α-aminobutyryl-sarcosyl-N-methyl-L-leucyl-4-fluoro-L-valyl-N-methyl-L-leucyl-L-alanine benzyl ester To a solution of Boc-D-Ala-MeLeu-MeLeu-MeValOH (prepared by the process set forth in R. M. Wenger, Helv. Chim. Acta. 66 (1983) 2672) (101 mg., 0.18 mmol.) and H-DMT-Abu-Sar-MeLeu-4-fluoroVal-MeLeu-AlaOBzl (140 mg., 0.15 mmol.) in dry dichloromethane (6 ml.) were added N-methylmorpholine (18 μl, 0.16 mmol.) and benzotriazol-1-yloxytris-(dimethylamino)phosphonium hexafluorophosphate (80 mg., 0.18 mmol). The reaction mixture was stirred 4 days at room temperature under a nitrogen atmosphere. It was then diluted with dichloromethane (100 ml.), washed with water (50 ml.), dried (sodium sulfate) and evaporated. The crude product was chromatographed on a column of silica gel (Merck #7734, packed as a slurry in 2% methanol in dichloromethane). Elution was effected with 2% methanol in dichloromethane. Fractions containing pure product were combined and evaporated to afford the desired Boc-D-Ala-MeLeu-MeLeu-MeVal-DMT-Abu-Sar-MeLeu-4-Fluoro-Val-MeLeu-AlaOBzl undecapeptide.

Step 11: Boc-D-Alanyl-N-methyl-L-leucyl-N-methyl-L-leucyl-N-methyl-L-valyl-((2S,3R,4S)-3-hydroxy-4-methyl-2-methylamino-6-methylthio)-pentanoyl-L-α-aminobutyryl-sarcosyl-N-methyl-L-leucyl-4-fluoro-L-valyl-N-methyl-L-leucyl-L-alanine To a solution of Boc-D-Ala-MeLeu-MeLeu-MeVal-DMT-Abu-Sar-MeLeu-4-Fluoro-Val-MeLeu-AlaOBzl (100 mg., 0.070 mmol.) in ethanol (4 ml.) cooled to ice temperature was added 0.2N aqueous sodium hydroxide (0.6 ml.). The reaction mixture was kept at 5° C. for 24 hours, brought to pH 5 with several drops of glacial acetic acid and then evaporated under diminished pressure. The residue was taken up in dichloromethane (25 ml.) and washed with water (12 ml.). The aqueous layer was extracted with dichloromethane, and the combined organic extracts were dried (sodium sulfate) and evaporated. The resulting material was applied to a column of silica gel (Merck #7734, packed as a slurry in 2% methanol in dichloromethane). Elution initially with 2% methanol in dichloromethane gave unreacted starting material and benzyl alcohol; subsequent elution with 15% methanol in dichloromethane afforded the partially protected Boc-D-Ala-MeLeu-MeLeu-MeVal-DMT-Abu-Sar-MeLeu-4-Fluoro-Val-MeLeu-AlaOH undecapeptide.

Step 12: D-Alanyl-N-methyl-L-leucyl-N-methyl-L-Leucyl-N-methyl-L-valyl-(2S,3R,4S)-3-hydroxy-4-methyl-2-(methylamino-5-(methylthio)-pentanoylacid-L-α-aminobutyryl-sarcosyl-N-methyl-L-leucyl-4-fluoro-L-valyl-N-methyl-L-leucyl-L-alanine Boc-D-Ala-MeLeu-MeLeu-MeVal-DMT-Abu-Sar-MeLeu-4-Fluoro-Val-MeLeu-AlaOH (60 mg., 0.045 mmol.) was cooled to −15° C. and treated with precooled trifluoroacetic acid (2.5 ml.) for 90 minutes at −15° C. The reaction mixture was then evaporated under diminished pressure (bath temperature of 0° C.) and co-evaporated several times with dichloromethane. The crude material was taken up in dichloromethane (25 ml.) and washed with saturated sodium hydrogencarbonate solution (12 ml.). The organic layer was dried (sodium sulfate) and evaporated. The product was triturated with diethyl ether and the resulting amorphous solid was filtered, washed with ether and dried in vacuo.

Step 13: Cyclo[-((2S,3R,4S)-N,4-Dimethyl-4-(methylthiomethyl)-threonyl)-L-α-aminobutyryl-sarcosyl-N-methyl-L-Leucyl-4-fluoro-Valyl-N-methyl-L-leucyl-Alanyl-D-Alanyl-N-methyl-L-leucyl-N-methyl-L-leucyl-N-methyl-L-Valyl]

Cyclization to the corresponding cyclosporin was then effected using the procedure of Example 1, Step 13.

While presently preferred embodiments of the invention have been described in detail for purposes of disclosure, numerous alternatives will readily suggest themselves to those skilled in the art and are encompassed within the principles of the invention and the scope of the appended claims.

What is claimed is:

1. A compound of the formula I

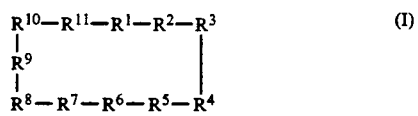

or a pharmaceutically acceptable salt thereof wherein
$R^1$ is MeBmt or dihydroMeBmt;
$R^2$ is Nva, Ser, Thr, or Val;
$R^3$ is Sar, or N-methyl-D-alanyl;
$R^4$ is MeLeu;
$R^5$ is Val or 4-fluoro-Val;
$R^6$ is MeLeu;
$R^7$ is Ala;
$R^8$ is D-alanyl;
$R^9$ is MeLeu;
$R^{10}$ is MeLeu; and
$R^{11}$ is MeVal or 4-fluoro-MeVal;
with the proviso that at least one of $R^5$ and $R^{11}$ is the amino acid residue with the 4-fluoro substituent.

2. A compound of Formula I

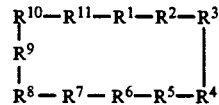

which is:
(a) $R^1$ is MeBmt, $R^2$ is Abut, $R^3$ is Sar, $R^4$ is MeLeu, $R^5$ is 4-fluoro-Val, $R^6$ is MeLeu, $R^7$ is Ala, $R^8$ is D-Ala, $R^9$ is MeLeu, $R^{10}$ is MeLeu, $R^{11}$ is MeVal;
(b) $R^1$ is dihydroMeBmt, $R^2$ is Abu, $R^3$ is Sar, $R^4$ is MeLeu, $R^5$ is 4-fluoro-Val, $R^6$ is MeLeu, $R^7$ is Ala, $R^8$ is D-Ala, $R^9$ is MeLeu, $R^{10}$ is MeLeu, $R^{11}$ is MeVal; or
(c) $R^1$ is MeBmt, $R^2$ is Abu, $R^3$ is Sar, $R^4$ is MeLeu, $R^5$ is Val, $R^6$ is MeLeu, $R^7$ is Ala, $R^8$ is D-Ala, $R^9$ is MeLeu, $R^{10}$ is MeLeu, $R^{11}$ is 4-fluoro-MeVal.

* * * * *